United States Patent
An et al.

(10) Patent No.: US 10,023,908 B2
(45) Date of Patent: Jul. 17, 2018

(54) NUCLEIC ACID AMPLIFICATION METHOD USING ALLELE-SPECIFIC REACTIVE PRIMER

(71) Applicant: Genomictree, Inc., Daejeon (KR)

(72) Inventors: Sung Whan An, Daejeon (KR); Tae Jeong Oh, Daejeon (KR)

(73) Assignee: Genomictree, Inc., Daejeon (KR)

( * ) Notice: Subject to any disclaimer, the term of this patent is extended or adjusted under 35 U.S.C. 154(b) by 306 days.

(21) Appl. No.: 14/779,356

(22) PCT Filed: Apr. 16, 2013

(86) PCT No.: PCT/KR2013/003185
§ 371 (c)(1),
(2) Date: Sep. 23, 2015

(87) PCT Pub. No.: WO2014/163225
PCT Pub. Date: Oct. 9, 2014

(65) Prior Publication Data
US 2016/0194695 A1      Jul. 7, 2016

(30) Foreign Application Priority Data

Apr. 1, 2013 (KR) .................. 10-2013-0035343

(51) Int. Cl.
C12Q 1/68      (2018.01)
C12Q 1/6858      (2018.01)

(52) U.S. Cl.
CPC .................. *C12Q 1/6858* (2013.01)

(58) Field of Classification Search
None
See application file for complete search history.

(56) References Cited

U.S. PATENT DOCUMENTS

| 5,487,972 A | 1/1996 | Gelfand et al. |
| 2006/0172307 A1 | 8/2006 | Li et al. |
| 2012/0230952 A1 | 9/2012 | Chung et al. |

FOREIGN PATENT DOCUMENTS

| JP | 2006-141255 A | 6/2006 |

OTHER PUBLICATIONS

Bi, W., et al., "Detection of known mutation by proof-reading PCR", Nucleic Acids Research, Jun. 15, 1998, pp. 3073-3075, vol. 26, No. 12.
Li, L., et al., "MethPrimer: designing primers for methylation PCRs", Bioinformatics, Nov. 2002, pp. 1427-1431, vol. 18, No. 11.
Li, X., et al., "A novel one cycle allele specific primer extension-molecular beacon displacement method for DNA point mutation detection with improved specificity", Analytica Chimica Acta, Nov. 11, 2006, pp. 12-18, vol. 584, No. 1.
Shendure, J., et al., "Next-generation DNA sequencing", Nature Biotechnology, Oct. 9, 2008, pp. 1135-1145, vol. 26, No. 10.
Di Giusto, D., et al., "Single Base Extension (SBE) with Proof-reading Polymerases and Phosphorothioate Primers: Improved Fidelity in Single-Substrate Assays", "Nucleic Acids Research", 2003, p. e7, vol. 31, No. 3.
Di Giusto, D., et al., "Strong Positional Preference in the Interaction of LNA Oligonucleotides with DNA Polymerase and Proofreading Exonuclease Activities: Implication for Genotyping Assays", "Nucleic Acids Research", Jan. 26, 2004, p. e32, vol. 32, No. 3.
Hu, Y.J., et al., "Enhanced Discrimination of Single Nucleotide Polymorphism in Genotyping by Phosphorothioate Proofreading Allele-Specific Amplification", "Analytical Biochemistry", May 3, 2007, p. 54-59, vol. 369.
Note: For the non-patent literature citations that no month of publication is indicated, the year of publication is more than 1 year prior to the effective filing date of the present application.

*Primary Examiner* — David C Thomas
(74) *Attorney, Agent, or Firm* — Hultquist, PLLC; Steven J. Hultquist

(57) ABSTRACT

A method is described for detecting a target nucleic acid, in which the target nucleic acid is amplified in the presence of a proofreading DNA polymerase and an allele-specific reactive primer (ASRP) including (i) a nucleotide sequence complementary to the target nucleic acid and (ii) modified nucleotide(s) located in a region from a nucleotide located right before a non-complementary nucleotide on the 5'-side of the non-complementary nucleotide, so that an amplification product of the target nucleic acid is produced when the ASRP is complementary to the target nucleic acid, and so that when the ASRP is not complementary to the target nucleic acid, an amplification product of the target nucleic acid will not be produced. The detection method has a very high specificity of amplification, and is useful for applications such as detecting mutations, detecting methylation of CpG after bisulfite treatment, and detecting target DNA from a DNA library.

23 Claims, 4 Drawing Sheets

M: 1kb ladder
1. Wild type/general primer
2. *BRAFV600E*/general primer
3. D.W
4. Wild type/ASRP
5. *BRAFV600E*/ASRP
6. D.W M: 1kb ladder
1. Methyl DNA/general primer
2. Unmethyl DNA/general primer
3. D.W
4. Methyl DNA/ASRP
5. Unmethyl DNA/ASRP
6. D.W

NUCLEIC ACID AMPLIFICATION METHOD USING ALLELE-SPECIFIC REACTIVE PRIMER

CROSS-REFERENCE TO RELATED APPLICATIONS

This application is a U.S. national phase under the provisions of 35 U.S.C. § 371 of International Patent Application No. PCT/KR13/03185 filed Apr. 16, 2013, which in turn claims priority of Korean Patent Application No. 10-2013-0035343 filed Apr. 1, 2013. The disclosures of such international patent application and Korean priority patent application are hereby incorporated herein by reference in their respective entireties, for all purposes.

TECHNICAL FIELD

The present invention relates to a method for amplifying nucleic acid using an allele-specific reactive primer (ASRP) designed to solve the problems of conventional allele-specific PCR, and more particularly, to a method for detecting a target nucleic acid, the method comprising amplifying the target nucleic acid in the presence of a DNA polymerase having proofreading activity, and an allele-specific reactive primer (ASRP) which comprises i) a nucleotide sequence complementary to the target nucleic acid and ii) one or more modified nucleotide(s) located in a region from a nucleotide located right before of a non-complementary nucleotide to 5' direction of the primer, which will be removed by the proofreading activity of the DNA polymerase when a non-complementary nucleotide is present at the 3' end, to a nucleotide located at the 5' end of the primer, in order for the nucleotide in the allele-specific reactive primer cannot act as a primer for a polymerase reaction.

BACKGROUND ART

A single nucleotide polymorphism (SNP) is a genetic variation in a DNA sequence that occurs when a single nucleotide is replaced by one of the other three nucleotides. It results in differences between individuals, such as pathogenic causes or responses to therapeutic drugs. The detection and identification of single nucleotide polymorphisms has received a lot of attention, because it is linked not only to personalized medicines, but also to new drug development.

For rapid detection of single nucleotide polymorphisms, various detection methods based on real-time PCR technology have been used. Typical examples of these detection methods include assays using DNA intercalating fluorescent dyes, assays using DNA probes, and assays using PNA probes. However these methods have shortcomings in that the use of DNA intercalating fluorescent dyes is limited and the use of a program for analyzing melting curves is required (Kirk M. Ririe et al., *Analytical Biochemistry* 245:154, 1997; U. Hladnik et al., *Clin Exp Med*, 2:105, 2002).

DNA polymerase with 3'→5' proofreading activity ensures high fidelity in DNA replication (Drake, J. W. et. al., *Cold Spring Harb. Symp. Quant. Biol.*, 33:339, 1968; Drake, J. W. et. al., *Nature*, 221:1128, 1968; Goodman, M. F. et. al. *Genetics*, 148:1475, 1998), and many proofreading polymerases with 3' exonuclease activity were been found.

DNA polymerase with proofreading activity ensures high fidelity in DNA replication in vivo, but when DNA polymerase with proofreading activity is applied to a polymerase chain reaction with conventional allele-specific primers, there is a problem in that, because a mismatched base at the 3' end is removed, the end of the primer is extended regardless of complete hybridization or incomplete hybridization of the primer with DNA used as a template (Zhang, J. et al., *Mol. Biotechnol.*, 24:105, 2003).

Due to this problem, activity of DNA polymerase with proofreading was hardly used in studies on the detection of mutations. However, in recent years, there have been studies on a method of detecting a mutation in a target nucleic acid using a method of modifying the 3' end of primers, such as a method of labeling the 3' end of the primers or conjugating a 3' exonuclease-resistant factor to the 3' end, or a method of removing the —OH group of the nucleotide at the 3' end or replacing the —OH group with other residue (Zhang, J. et al., *Current Drug Disc.*, 9:21, 2001; Bi, W. L. and Sambrook, P. J., *Nucleic Acids Res.*, 26:3073, 1998).

For example, in the case in which the 3' end of a primer is labeled, when the primer binds complementarily to the template DNA, a final amplification product is produced while the label at the 3' end is maintained, but when the primer mismatches the template DNA, the label at 3' end is removed by the proofreading activity of DNA polymerase with proofreading, and thus a final amplification product free of the label is produced, indicating that a mutation can be detected on the presence or absence of the label. Based on this principle, allele-specific primers having 3' ends modified in various ways, and DNA polymerase with proofreading activity, can be applied to various platforms, including real-time PCR, multi-well plate and microarray techniques.

Accordingly, the present inventors have made extensive efforts to detect a target nucleic acid using a 3' end-modified primer and a DNA polymerase having proofreading activity, and as a result, have found that a target nucleic acid is specifically amplified using an allele-specific reactive primer (ASRP) in which a nucleotide at the 3' end is modified, in the presence of a DNA polymerase having proofreading activity, thereby completing the present invention.

DISCLOSURE OF INVENTION

Technical Problem

It is an object of the present invention to provide a method of detecting a target nucleic acid using an allele-specific reactive primer (ASRP) which comprises a nucleotide sequence complementary to the target nucleic acid and in which one or more modified nucleotide(s) located in a region from a nucleotide located right before of a non-complementary nucleotide to 5' direction of the primer, which will be removed by the proofreading activity of the DNA polymerase when a non-complementary nucleotide is present at the 3' end, to a nucleotide located at the 5' end of the primer, in order for the nucleotide in the allele-specific reactive primer cannot act as a primer for a polymerase reaction, and a method for selectively amplifying a target nucleic acid from a DNA library.

Technical Solution

To achieve the above object, the present invention provides a method for detecting a target nucleic acid, the method comprising amplifying the target nucleic acid in the presence of a DNA polymerase having proofreading activity and an allele-specific reactive primer (ASRP) which comprises i) a nucleotide sequence complementary to the target nucleic acid and ii) one or more modified nucleotide(s)

located in a region from a nucleotide located right before of a non-complementary nucleotide to 5' direction of the primer, which will be removed by the proofreading activity of the DNA polymerase when a non-complementary nucleotide is present at the 3' end, to a nucleotide located at the 5' end of the primer, in order for the nucleotide in the allele-specific reactive primer cannot act as a primer for a polymerase reaction.

The present invention also provides a method of amplifying a target nucleic acid starting with a specific nucleotide sequence from a DNA library, the method comprising amplifying the target nucleic acid from the DNA library in the presence of a DNA polymerase having proofreading activity and an allele-specific reactive primer (ASRP) which comprises a nucleotide sequence complementary to an adaptor sequence of DNA library at its 5' end, and at 3' end a nucleotide sequence complementary to the target nucleic acid and modified nucleotide(s) in order for the nucleotide in the allele-specific reactive primer cannot act as a primer for a polymerase reaction.

The present invention also provides a method for detecting a target nucleic, the method comprising amplifying the target nucleic acid in the presence of: (i) an allele-specific reactive primer (ASRP) comprising, a tagging sequence comprising a nucleotide sequence non-complementary to the target nucleic acid at its 5' end, a modified single nucleotide and a nucleotide sequence complementary to the target nucleic acid, the allele-specific reactive primer (ASRP) having one or more modified nucleotide(s) at a 3' end, in order for the nucleotide in the allele-specific reactive primer cannot act as a primer for a polymerase reaction; (ii) a tagging sequence and a reporter template comprising a portion of the nucleotide sequence complementary to the target nucleic acid; and (iii) a DNA polymerase having 3'→5' exonuclease activity.

BEST MODE FOR CARRYING OUT THE INVENTION

Figure 1:
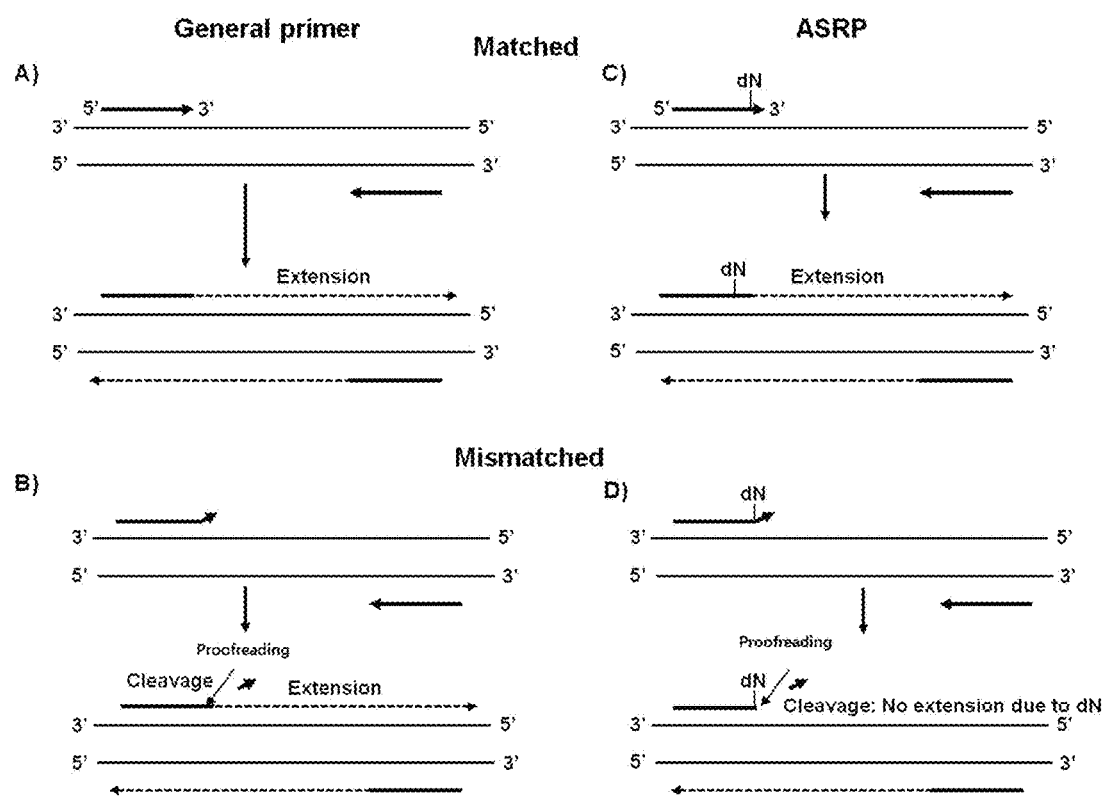
FIG. 1 is a schematic diagram showing a detection system utilizing an allele-specific reactive primer (ASRP).

Unless otherwise defined, all technical and scientific terms used herein have the same meaning as commonly understood by one of ordinary skill in the art to which the invention pertains. Generally, the nomenclature used herein are well known and commonly used in the art.

In one aspect, the present invention is directed to a method for detecting a target nucleic acid, the method comprising amplifying the target nucleic acid in the presence of a DNA polymerase having proofreading activity, and an allele-specific reactive primer (ASRP) which comprises i) a nucleotide sequence complementary to the target nucleic acid and ii) one or more modified nucleotide(s) located in a region from a nucleotide located right before of a non-complementary nucleotide to 5' direction of the primer, which will be removed by the proofreading activity of the DNA polymerase when a non-complementary nucleotide is present at the 3' end, to a nucleotide located at the 5' end of the primer, in order for the nucleotide in the allele-specific reactive primer cannot act as a primer for a polymerase reaction.

The allele-specific reactive primer (hereinafter, referred to as "ASRP") that is used in the present invention is a primer designed to solve the problems of conventional allele-specific PCRs. According to the present invention, a target nucleic acid can be specifically amplified using a DNA polymerase having proofreading activity and an allele-specific reactive primer which comprises a nucleotide sequence complementary to the target nucleic acid so as to be capable of specifically amplifying a desired allele and one or more modified nucleotide(s) located in a region from a nucleotide located right before of a non-complementary nucleotide to 5' direction of the primer, which will be removed by the proofreading activity of the DNA polymerase when a non-complementary nucleotide is present at the 3' end, to a nucleotide located at the 5' end of the primer, in order for the nucleotide in the allele-specific reactive primer cannot act as a primer for a polymerase reaction.

As used herein, the term "target nucleic acid" refers to the nucleic acid sequence (DNA or RNA) to be detected, and the target nucleic acid is hybridized to a primer or a probe under hybridization, annealing or amplification conditions. The term "target nucleic acid" is used interchangeably with the term "target nucleic acid sequence" or "target sequence" as used herein.

As used herein, the term "hybridization" means that complementary single-stranded nucleic acids form a double-stranded nucleic acid. Hybridization can occur when the complementarity between two nucleic acid strands is perfect (perfect match) or when some mismatched residues exist. The complementarity level for hybridization may vary depending on hybridization conditions, particularly temperature.

In the present invention, the allele-specific reactive primer is characterized in that, if a nucleotide located next 3' side to the modified nucleotide of the allele-specific reactive primer is complementary to a target nucleic acid, it is not removed by the proofreading activity of DNA polymerase, and if the nucleotide is not complementary to the target nucleic acid, it is removed by the proofreading activity of DNA polymerase, and thus the modified nucleotide remains at the 3' end.

In the present invention, the DNA polymerase having proofreading activity may have 3'→5' exonuclease activity.

In the present invention, the modified nucleotide such that the nucleotide in the allele-specific reactive primer cannot act as a primer for a polymerase reaction, may be substituted nucleotide with at least one selected from the group consisting of deoxynucleotide and inverted (reverse) deoxynucleotide. In an example of the present invention, an ASRP in which the nucleotide at the 3' end is substituted with deoxynucleotide was used, but is not limited and any conventional nucleotide modification method known in the art may be used.

The method for detecting a target nucleic acid according to the present invention specifically comprises the steps of: (a) mixing and hybridizing the target nucleic acid to an allele-specific reactive primer (ASRP) to obtain a hybridization product; (b) amplifying the target nucleic acid in the hybridization product in the presence of a DNA polymerase having proofreading activity; and (c) detecting the target nucleic acid based on the presence or absence of an amplification product of the target nucleic acid.

In the present invention, for target-specific amplification in the presence of ASRP, a DNA polymerase with 3'→5' proofreading exonuclease should be used. In the presence of the enzyme DNA polymerase, when a general primer binds to a template DNA (target nucleic acid) and if the 3' end of the primer is complementary to the template DNA, a DNA polymerase reaction proceeds in the 5'→3' direction without proofreading (FIG. 1A), whereas when one or more nucleotides at the 3' end is not complementary to the template, a proofreading reaction that cleaves all the nucleotides is performed regardless of the number of the non-complementary nucleotides, and then a new nucleotide sequence complementary to the template is synthesized (FIG. 1B). In the case in which the ASRP according to the present invention is used, when the 3' end of the primer is complementary to the template, a DNA polymerase reaction proceeds in the 5'→3' direction without proofreading (FIG. 1C), like the use of the general primer, whereas when the nucleotides at the 3' end are not complementary to the template, all the non-complementary nucleotides are removed by a proofreading reaction regardless of the number of the non-complementary nucleotides (FIG. 1D). After completion of the proofreading reaction, deoxynucleotide remains at the 3' end, and the DNA polymerase reaction is stopped, because the ASRP having this structure cannot act as a primer for a polymerase reaction. Thus, when a combination of a DNA polymerase having proofreading activity and the ASRP is used to induce a DNA polymerase reaction, only a template DNA having a specific sequence can be selectively amplified, because the ASRP causes the polymerase reaction only when it meets a template complementary thereto.

In the present invention, the concentration of the allele-specific reactive primer (ASRP) may be 0.1-20 M, and the amplification in step (b) may be performed by Polymerase chain reaction (PCR).

In the present invention, if the allele-specific reactive primer is complementary to the target nucleic acid, an amplification product of the target nucleic acid is produced (Match/On), and if the allele-specific reactive primer is not complementary to the target nucleic acid, the mismatched nucleotides are removed by the proofreading activity of the DNA polymerase, and the amplification product of the target nucleic acid is not produced due to the modified nucleotide remaining at the 3' end of the primer (Mismatch/Off).

In the present invention, the target nucleic acid may be DNA or RNA, and a mutation or a pathogen can be detected using the target nucleic acid detection method of the present invention.

When the method of the present invention is used to detect a mutation, not only a single nucleotide polymorphism, but also a mutation caused by the substitution, deletion or insertion of a nucleotide of the target nucleic acid, can be detected. In addition, if no mutation is present in the target nucleic acid, an amplification product of the target nucleic acid will be produced, and if a mutation is present in the target nucleic acid, the amplification product of the target nucleic acid will not be produced.

Figure 2:
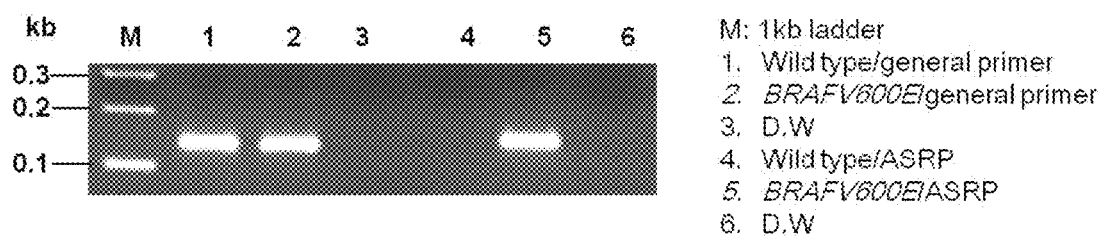
FIG. 2 shows the results of performing PCR amplification experiments using a general primer and the ASRP in order to detect a single nucleotide mutation.

In an example of the present invention, in order to detect a mutation using the allele-specific reactive primer (ASRP) of the present invention, an experiment on the detection of the BRAFV600E somatic point mutation that is a typical cancer cell mutation was performed. As a result, it could be seen that, when a general primer was used, not only amplification of the BRAFV600E mutation (lane 2 in FIG. 2), but also non-specific amplification of wild-type BRAF (lane 1 in FIG. 2) occurred. However, when PCR was performed using the ASRP, wild-type BRAF used as a template was not amplified (lane 5 in FIG. 2), and only the BRAFV600E mutation used as a template was amplified (lane 4 in FIG. 2).

The method of detecting a pathogen using the method of the present invention is characterized in that an amplification product of the target nucleic acid is produced in the presence of a pathogen, and is not produced in the absence of a pathogen. The pathogen that is used in the present invention is a disease-causing microorganism, and may be selected from the group consisting of viruses, eubacteria, fungi, and protozoa, but is not limited thereto, and includes any organism that infects humans or animals to directly cause disease.

In addition, the target nucleic acid detection method of the present invention can be used to detect a cytosine-methylated gene. In this case, an amplification product of a methylated target nucleic acid is produced, and an amplification product of an unmethylated target nucleic acid is not produced.

As used herein, the term "methylation" means that a methyl group is attached to the 5-carbon of the cytosine ring to form 5-methylcytosine (5-mC). 5-methylcytosine is always attached only to the C of a CG dinucleotide (5'-mCG-3'), and this CG is frequently expressed as CpG. Methylation of this CpG inhibits the expression of a repetitive sequence in genomes, such as alu or transposon. In addition, CpG is a site where an epigenetic change in mammal cells occurs most often. The 5-mC of this CpG is naturally deaminated to T, and thus the CpG in mammal genomes shows a frequency of only 1%, which is much lower than a normal frequency ($¼ \times ¼ = 6.25\%$).

Regions in which CpG is exceptionally integrated are known as CpG islands. The CpG islands refer to sites which are 0.2-3 kb in length, and have a C+G content of more than 50% and a CpG ratio of more than 3.75%. There are about 45,000 CpG islands in the human genome, and they are mostly found in promoter regions regulating the expression of genes. Actually, the CpG islands occur in the promoters of housekeeping genes accounting for about 50% of human genes (Cross, S. & Bird, A. P., *Curr. Opin. Gene Develop.*, 5:309, 1995).

The method for detecting a methylated target nucleic acid according to the present invention specifically comprises the steps of: (a) chemically or enzymatically treating the target nucleic acid to covert an unmethylated cytosine nucleotide into uracil or other nucleotides than cytosine without converting a methylated cytosine nucleotide; (b) mixing and hybridizing the chemically or enzymatically treated target nucleic acid to an allele-specific reactive primer (ASRP) to obtain a hybridization product, and amplifying the target product in the hybridization product in the presence of a DNA polymerase having proofreading activity; and (c) detecting methylation of the target nucleic acid based on the presence or absence of an amplification product of the target nucleic acid.

The method of detecting methylation of the target nucleic acid using the ASRP according to the present invention comprises a step of chemically or enzymatically treating the target nucleic acid to covert an unmethylated cytosine nucleotide into uracil or other nucleotides than cytosine without converting a methylated cytosine nucleotide. For detection of a methylated nucleic acid, a DNA polymerase with 3'→5' proofreading exonuclease should be used. When a general primer binds to a template and the 3' end of the primer is complementary to a methylated target nucleic acid, a DNA polymerase reaction proceeds in the 5'→3' direction without proofreading. When an unmethylated cytosine nucleotide is converted into uracil or other nucleotides than cytosine, even if the nucleotide at the 3' end is not complementary to the template, a proofreading reaction that cleaves the non-complementary nucleotide by the proofreading activity of the DNA polymerase is performed, and then a new nucleotide sequence complementary to the template is synthesized.

In the case in which the ASRP according to the present invention is used, when the 3' end of the primer is complementary to the methylated target nucleic acid, a DNA polymerase reaction proceeds in the 5'→3' direction without proofreading, whereas when an unmethylated cytosine nucleotide is converted into uracil or other nucleotides than cytosine and the nucleotides at the 3' end of the primer are not complementary to the template, the non-complementary nucleotides are removed by the proofreading reaction of the DNA polymerase. After completion of the proofreading reaction, deoxynucleotide remains at the 3' end, and the DNA polymerase reaction is stopped, because the ASRP having this structure cannot act as a primer for the DNA polymerase reaction.

In another example of the present invention, in order to detect a methylated gene using the allele-specific reactive primer (ASRP) of the present invention, an experiment on the detection of methylation of human SDC2 gene was performed. As a result, it was shown that, when a general primer was used, an amplification product appeared in both methylated SDC2 (lane 1 in FIG. 3) and unmethylated SDC2 (lane 2 in FIG. 3) even when a methylation-specific primer was used, whereas when an SDC2 methylation-specific ASRP was used, a specific amplification product was observed in methylated SDC2 (lane 4 in FIG. 3), but no amplification occurred in unmethylated SDC2 (lane 5 in FIG. 3).

In the present invention, a compound for converting an unmethylated cytosine nucleotide into uracil may be bisulfite. SDC2 used in an example of the present invention was a gene synthesized using a nucleotide sequence in which a cytosine nucleotide was changed to uracil, and a bisulfite treatment process was omitted in the example.

In another aspect, the present invention is directed to a method of amplifying a target nucleic acid starting with a specific nucleotide sequence from a DNA library, the method comprising amplifying the specific nucleic acid from the DNA library in the presence of a DNA polymerase having proofreading activity and an allele-specific reactive primer (ASRP) which comprises, at its 5' end, a nucleotide sequence complementary to the adaptor sequence of the DNA library, and comprises, at its 3' end, a nucleotide sequence complementary to the target nucleic acid and modified nucleotide(s) in order for the nucleotide in the allele-specific reactive primer cannot act as a primer for a polymerase reaction.

As used herein, the term "DNA library" refers to a collection of a sufficient number of clones so that it includes all single genes present in a specific organism. A genomic DNA library is constructed by isolating total cell DNA, partially digesting the isolated DNA and cloning the produced fragments into vectors. As the vector, BAC, YAC, Fosmid, Cosmid or the like, into which a larger gene or a gene cluster can be cloned, is used, although a plasmid that has been generally used is also used.

In the present invention, a DNA fragment comprising the nucleotide sequence of a target nucleic acid can be selectively amplified from a DNA library. According to the method of the present invention, a target nucleic acid having a specific nucleotide sequence can be amplified from a next-generation sequencing (NGS) library using an allele-specific specific reactive primer.

The method of amplifying a target nucleic acid having a specific nucleotide sequence from a DNA library according to the present invention specifically comprises the steps of: (a) randomly digesting a genomic DNA, and linking a sequencing adaptor sequence to both the 5' and 3' ends of the digested DNA fragments to prepare a DNA library; (b) mixing and hybridizing DNA library with an allele-specific reactive primer (ASRP), wherein the allele-specific reactive primer (ASRP) comprises a nucleotide sequence complementary to the adaptor sequencer of the DNA library and one or more modified nucleotide(s) located in a region from a nucleotide located right before of a non-complementary nucleotide to 5' direction of the primer, which will be removed by the proofreading activity of the DNA polymerase when a non-complementary nucleotide is present at the 3' end, to a nucleotide located at the 5' end of the primer, in order for the nucleotide in the allele-specific reactive primer cannot act as a primer for a polymerase reaction; and (c) performing amplification starting from a specific nucleotide sequence in the hybridization product in the presence of a DNA polymerase having proofreading activity. In the method, if the target nucleic acid is present in the DNA library, it binds complementarily to the allele-specific reactive primer to produce an amplification product, and if the target nucleic acid is not complementary to the allele-specific reactive primer, the non-complementary nucleotide is removed by the proofreading activity of the DNA polymerase, and an amplification product is not produced due to the remaining modified nucleotides at the 3' end.

Figure 4:
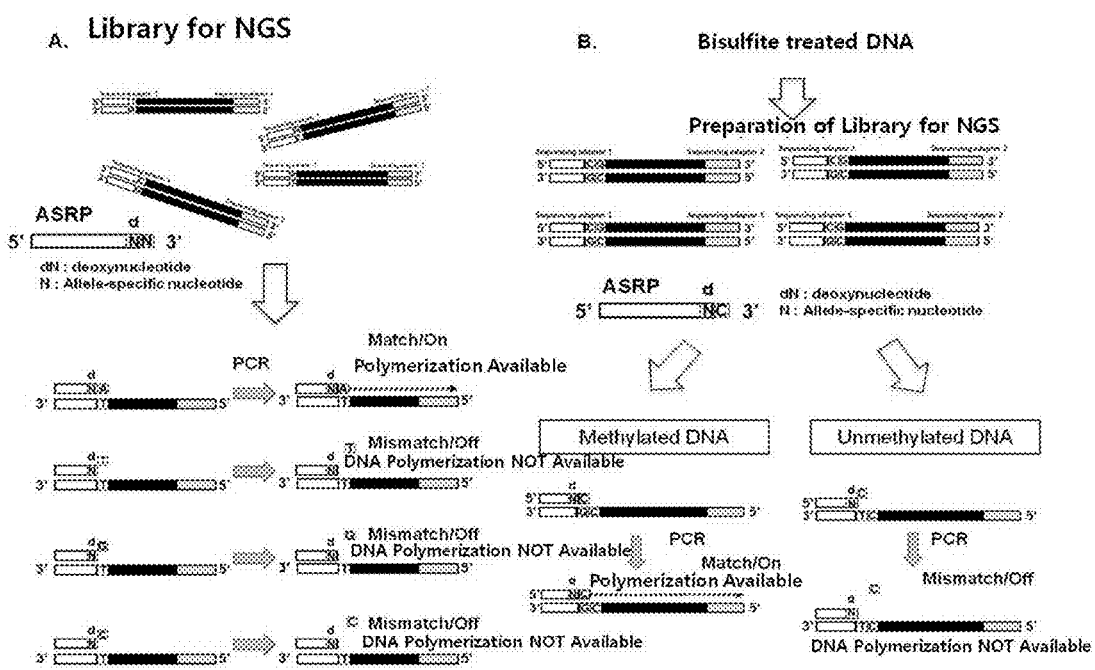
FIG. 4 is a schematic diagram showing a process of amplifying a target DNA starting with a desired nucleotide sequence from a DNA library using an allele-specific reactive primer (ASRP).

According to the method of the present invention, next-generation sequencing (NGS) can be performed by randomly digesting a genomic DNA to prepare DNA fragments, linking a sequencing adaptor sequence to both the 5' and 3' ends of the DNA fragments to construct a DNA library, and selectively amplifying DNA fragments having a specific nucleotide sequence from the DNA library. As shown in FIG. 4A, a library is constructed, when one or more of nucleotides located at 3'side of modified nucleotide, selected among nucleotides including $2^{nd}$ nucleotide to a nucleotide at 5' end of adaptor for sequencing, is non-complementary, for example, if N (; A, T, C, G) ($1^{st}$ nucleotide located right before of nucleotide at end of the adaptor sequence) is complementary to ASRP, the library is amplified without proofreading, if not complementary, the nucleotide is removed by proofreading and the polymerization does not occur. Therefore, according to this process, only DNA fragments containing a genomic DNA fragment starting from a specific nucleotide can be selectively amplified from a DNA library.

According to the present invention, a methylated target nucleic acid can be amplified from a DNA library. Specifically, the method for amplification of a methylated target nucleic acid comprises the steps of: (a) chemically or enzymatically treating a genomic DNA to convert an unmethylated cytosine nucleotide into uracil or other nucleotides without converting a methylated cytosine nucleotide; (b) randomly digesting the genomic DNA, and linking a sequencing adaptor to both the 5' and 3' ends of the digested DNA fragments to construct a DNA library; (c) mixing and hybridizing DNA library with an allele-specific reactive primer (ASRP), wherein the ASRP comprises a nucleotide sequence complementary to the adaptor sequence of the DNA library and at the 3' end, a cytosine and one or more modified nucleotide(s) in order for the nucleotide in the allele-specific reactive primer cannot act as a primer for a polymerase reaction; and (d) amplifying a DNA fragment comprising the nucleotide sequence of a methylated target nucleic acid in the hybridization product in the presence of a DNA polymerase having proofreading activity, wherein a methylated target nucleic acid is amplified and an unmethylated target nucleic acid is not amplified.

When next-generation sequencing (NGS) is to be performed after the treatment of a genomic DNA with bisulfite, the next-generation sequencing (NGS) can be performed by selectively amplifying DNA fragments having a methylated nucleotide sequence using the method of the present invention from a library constructed by linking a sequencing sequence to both the 5' and 3' ends. As shown in FIG. 4B, when a library constructed using a bisulfite-treated genomic DNA is amplified with a DNA polymerase having proofreading activity using an ASRP prepared to have an adaptor sequence at the 5' end and a deoxynucleotide-modified nucleotide sequence and a methylated cytosine (C) sequence at the 3' end, if the first nucleotide of the DNA fragment in the DNA library is a methylated cytosine, the DNA fragment is amplified without proofreading, and if the nucleotide is not complementary, it is removed by a proofreading reaction, and the DNA fragment is not amplified due to the remaining modified nucleotide at the 3' end. Therefore, according to this process, DNA fragments comprising a methylated DNA fragment can be selectively amplified from a DNA library.

In still another aspect, the present invention is directed to a method for detecting a target nucleic, the method comprising amplifying the target nucleic acid in the presence of: (i) an allele-specific reactive primer (ASRP) comprising, at its 5' end, a tagging sequence comprising a nucleotide sequence non-complementary to the target nucleic acid, a modified single nucleotide and a nucleotide sequence complementary to the target nucleic acid, the allele-specific reactive primer (ASRP) having a 3' end modified such that the primer cannot act as a primer for DNA polymerase; (ii) a reporter template comprising a tagging sequence and a portion of the nucleotide sequence complementary to the target nucleic acid; and (iii) a DNA polymerase having 3'→5' exonuclease activity.

In the present invention, the tagging sequence of the allele-specific reactive primer may consist of 15-30 nucleotides, and the modified single nucleotide cannot act as a primer for DNA polymerase.

The reporter template according to the present invention comprises, at the 3' end, a nucleotide sequence capable of binding to the tagging sequence and a single nucleotide (N: A, T, C or G) capable of binding complementarily to a nucleotide sequence complementary to the target nucleic acid (target-specific sequence), and comprises, at the 5' end, an artificial sequence having a size of 20 bp or more.

The method for detecting a target nucleic acid according to the present invention specifically comprises the steps of: (a) mixing and hybridizing the target nucleic acid to: (i) an allele-specific reactive primer (ASRP) which comprises, a tagging sequence comprising a nucleotide sequence non-complementary to the target nucleic acid at 5' end, a modified single nucleotide and a nucleotide sequence comple-mentary to the target nucleic acid, and has one or more modified nucleotide(s) at 3' end, in order for the nucleotide in the allele-specific reactive primer cannot act as a primer for a polymerase reaction; (ii) a tagging sequence and a reporter template comprising a portion of the nucleotide sequence complementary to the target nucleic acid; and (iii) a primer complementary to the target nucleic acid; (b) removing a portion of the allele-specific reactive primer, which includes the 5'-end tagging sequence that does not hybridize to the target nucleic acid, by a DNA polymerase having 3'→5' exonuclease activity, followed by hybridization to the reporter template; and (c) amplifying the hybridized reporter template, and detecting the target nucleic acid based on the presence or absence of an amplification product of the reporter template. In this method, if the target nucleic acid is not present or the target nucleic acid contains a mutation, an amplification product of the reporter template is produced, and if the target nucleic acid is present, the amplification product is not produced.

Figure 5:
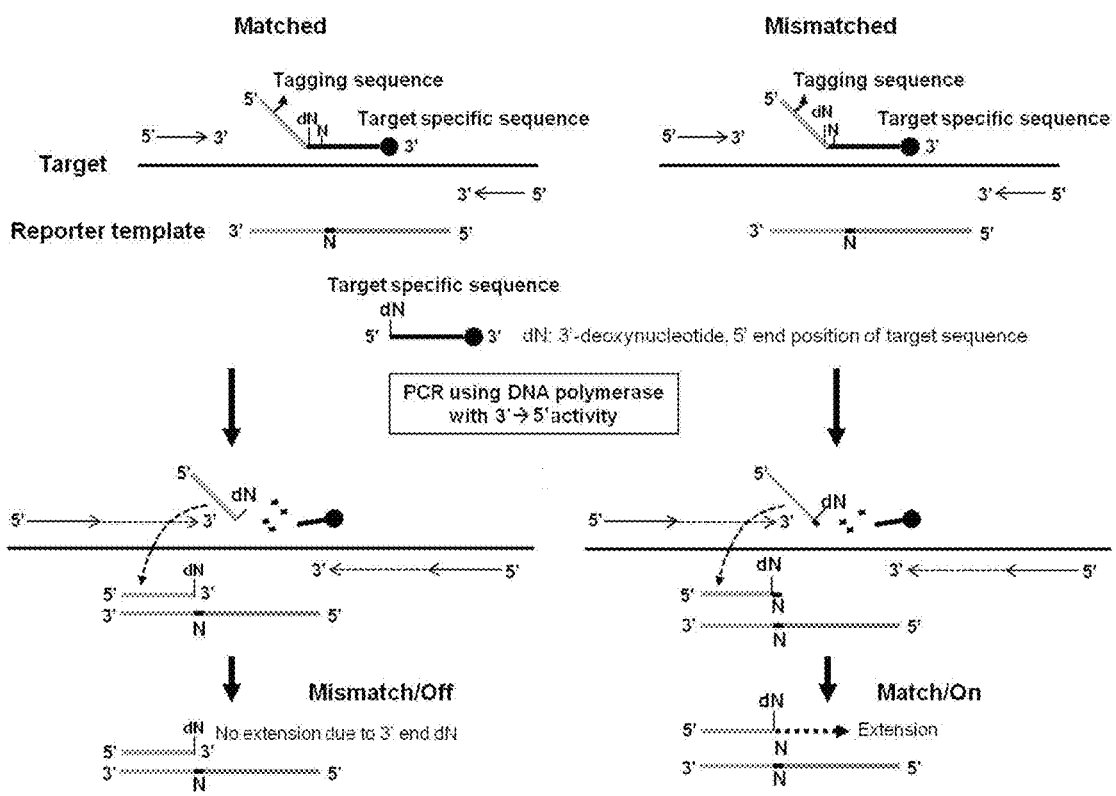
FIG. 5 is a schematic diagram showing a detection system that uses an allele-specific reactive primer (ASRP) comprising a tagging sequence, a modified single nucleotide and a target-specific sequence complementary to a target nucleic acid, and a DNA polymerase having 3'→5' exonuclease activity and no proofreading activity.

As shown in FIG. 5, in the present invention, to perform PCR using a DNA polymerase having 3'→5' exonuclease activity, an allele-specific reactive primer capable of binding complementarily to the middle portion of a template (target nucleic acid) was constructed in addition to both end primers. The allele-specific reactive primer of the present invention has a 3' end modified such that it cannot act as a primer for DNA polymerase and a primer in a PCR reaction. To the 5' end of the allele-specific reactive primer is linked a tagging sequence that binds to a reporter template for use as a template for secondary PCR and that can act as a PCR primer. To the tagging sequence, a single nucleotide modified into deoxynucleotide (dN: dA, dT, dG or dC), and a nucleotide sequence complementary to the target nucleic acid (target-specific sequence) are linked.

In the present invention, if the nucleotide (N) located at the 3' side of the modified single nucleotide (dN) of the allele-specific reactive primer matches the target nucleic acid, a fragment comprising the modified single nucleotide (dN) linked to the 3' end of the tagging sequence is made by the DNA polymerase having 3'→5' exonuclease activity. This fragment can bind complementarily to the reporter template, but the amplification of the fragment does not occur and an amplification product of the fragment is not produced, because the nucleotide at the 3' end is modified into deoxynucleotide. However, the nucleotide (N) located at the 3' side of the modified single nucleotide (dN) of the allele-specific reactive primer mismatches the nucleotide sequence of the target nucleic acid due to a mutation of the target nucleic acid, the modified single nucleotide (dN) at the 3' end of the tagging sequence and the nucleotide (N: A, T, G or C) located at the 3' side of the modified single nucleotide (dN) are removed in a linked state by the DNA polymerase having 3'→5' exonuclease activity, and thus a fragment capable of binding complementarily to the reporter plate is made. This fragment binds complementarily to the reporter template, and a general nucleotide (N), not a modified nucleotide, is attached to the 3' end of the fragment. Thus, the amplification of the fragment occurs and an amplification product of the fragment is produced.

In the present invention, the target nucleic acid may be DNA or RNA, and the target nucleic acid detection method of the present invention can be used to detect a mutation.

When the method of the present invention is used to detect a mutation, not only a single nucleotide polymorphism, but also a mutation caused by the substitution, deletion or insertion of a nucleotide, can be detected. In addition, if no mutation is present in the target nucleic acid, an amplification product of the reporter template is produced, and if a mutation is present in the target nucleic acid, the amplification product of the reporter template is not produced.

A kit containing the allele-specific reactive primer (ASRP) of the present invention can be prepared. The kit can be configured in various ways depending on the intended use. Preferably, the kit may be used for detection of a mutation in a target nucleic acid, detection of methylation of a target nucleic acid, and selective amplification of a target nucleic acid from a DNA library.

The kit of the present invention may comprise a DNA polymerase having proofreading activity or a DNA polymerase having 3'→5' exonuclease activity depending on the intended use, and may optionally comprise reagents required for target amplification PCR reaction (e.g., PCR reaction), such as buffer and deoxyribonucleotide-5-triphosphate. Optionally, the kit of the present invention may also comprise various polynucleotide molecules, various buffers, reagents, and antibodies for inhibiting DNA polymerase activity.

In the kit, the optimum amount of reagents for use in specific reactions can be determined by those skilled in the art from the disclosure of the specification. Typically, the kit of the present invention is prepared as a separate package or compartment containing the above-mentioned components.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Detection of BRAFV600E Mutation Using ASRP

In order to detect a mutation using the allele-specific reactive primer (ASRP) of the present invention, an experiment on the detection of the (BRAFV600ET1799A) somatic point mutation that is a typical cancer cell mutation was performed.

To prepare a mutation (BRAFV600E (SEQ ID NO: 2) of wild-type BRAF (B-type Raf kinase; SEQ ID NO: 1), a BRAFV600E gene having a T-to-A mutation was synthesized (Bioneer, Korea), and cloned into a pTOP TA V2 plasmid vector (Enzynomics, Korea) using a TOPcloner TA core kit (Enzynomics, Korea) (Bioneer, Korea). For amplification of the BRAFV600E point mutation, a forward general primer (SEQ ID NO: 3) having a sequence complementary to BRAFV600E, a forward ASRP primer (SEQ ID NO: 4) having a sequence complementary to BRAFV600E and having a substitution of deoxyguanine (dG) for the $2^{nd}$ nucleotide at the 3' end, and a reverse primer having a sequence complementary to BRAFV600E (SEQ ID NO: 5) were synthesized (Bioneer, Korea):

$10^5$ copies of wild-type BRAF and BRAFV600E mutant plasmids were used as templates for PCR amplification, and as a DNA polymerase having 3'→5' proofreading activity, Pfu polymerase (HelixAmp™ Power-Pfu Polymerase, Nanohelix, Korea) was used. PCR was performed using Veriti® thermal cycler (Applied Biosystems, Singapore), and PCR conditions were as follows. $10^5$ copies of a template, 2.5 μl of 10× Power-pfu buffer, 1 μl of dNTP mix (10 mM), 1 μl of each primer (4 pmole/ul), and Pfu polymerase (HelixAmp™ Power-Pfu Polymerase, 1.25 units) were added to a total volume of 25 μl, and then PCR was performed under the conditions shown in Table 1 below.

TABLE 1

| PCR reaction conditions | | |
| --- | --- | --- |
| Temperature | Reaction time | |
| 95° C. | 5 min | 1 cycle |
| 95° C. | 20 sec | 40 cycle |
| 59° C. | 40 sec | |
| 72° C. | 40 sec | |
| 72° C. | 5 min | 1 cycle |

10 μl of the PCR reaction product was mixed with 5×DNA loading dye and loaded onto 3% agarose gel (SeaKem LE Agarose, USA), and the size of the amplification product was analyzed.

As a result, it could be seen that, when the general primer was used, not only amplification of the BRAFV600E mutation (lane 2 in FIG. 2), but also non-specific amplification of wild-type BRAF (lane 1 in FIG. 2) occurred. However, when PCR was performed using the ASRP, wild-type BRAF used as a template was not amplified (lane 5 in FIG. 2), and only the BRAFV600E mutation used as a template was amplified (lane 4 in FIG. 2).

Example 2: Detection of Methylation Using ASRP

In order to detect a methylated gene using the allele-specific reactive primer (ASRP) of the present invention, an experiment on the detection of methylation of human SDC2 gene was performed.

A methylated SDC2 (Syndecan-2) nucleotide sequence (SEQ ID NO: 6) and an unmethylated SDC2 nucleotide sequence (SEQ ID NO: 7) were constructed by a gene synthesis method (Bioneer, Korea), and cloned into pTOP TA V2 plasmid vectors (Enzynomics, Korea) using a TOPcloner TA core kit (Enzynomics, Korea) (Bioneer, Korea). For amplification of methylated SDC2, a forward general primer (SEQ ID NO: 8) having a sequence complementary to methylated SDC2, a forward ASRP primer (SEQ ID NO: 9) having a sequence complementary to methylated SDC2 and having a substitution of deoxyguanine; dG) for the $2^{nd}$ nucleotide of the 3' end, and a reverse primer (SEQ ID NO: 10) having a sequence complementary to methylated SDC2, were synthesized:

[SEQ ID NO: 3]
5'-GTGATTTTGGTCTAGCTACAGA-3'

[SEQ ID NO: 4]
5'-GTGATTTTGGTCTAGCTACA[dG]A-3'

[SEQ ID NO: 5]
5'-TTCTAGTAACTCAGCAGCATCTC-3'

[SEQ ID NO: 8]
5'-TAGAAATTAATAAGTGAGAGGGC-3'

[SEQ ID NO: 9]
5'-TAGAAATTAATAAGTGAGAGG[dG]C-3'

[SEQ ID NO: 10]
5'-GACTCAAACTCGAAAACTC-3'

10⁵ copies of methylated SDC2 and unmethylated SDC2 plasmids were used as templates for PCR amplification, and as a DNA polymerase having 3'→5' proofreading activity, Pfu polymerase (HelixAmp™ Power-Pfu Polymerase, Nanohelix, Korea) was used. PCR was performed using Veriti® thermal cycler (Applied Biosystems, Singapore), and PCR conditions were as follows. 10⁵ copies of a template, 2.5 µl of 10× Power-pfu buffer, 1 µl of dNTP mix (10 mM), 1 µl of each primer (4 pmole/ul), and Pfu polymerase (HelixAmp™ Power-Pfu Polymerase, 1.25 units) were added to a total volume of 25 µl, and then PCR was performed under the conditions shown in Table 2 below.

TABLE 2

PCR reaction conditions

| Temperature | Reaction time | |
|---|---|---|
| 95° C. | 5 min | 1 cycle |
| 95° C. | 20 sec | 40 cycle |
| 59° C. | 40 sec | |
| 72° C. | 40 sec | |
| 72° C. | 5 min | 1 cycle |

10 µl of the PCR reaction product was mixed with 5×DNA loading dye and loaded onto 3% agarose gel (SeaKem LE Agarose, USA), and the size of the amplification product was analyzed.

As a result, it could be seen that, when the general primer was used, not only amplification of the BRAFV600E mutation (lane 2 in FIG. 2), but also non-specific amplification of wild-type BRAF (lane 1 in FIG. 2) occurred. However, when PCR was performed using the ASRP, wild-type BRAF used as a template was not amplified (lane 5 in FIG. 2), and only the BRAFV600E mutation used as a template was amplified (lane 4 in FIG. 2).

Figure 3:
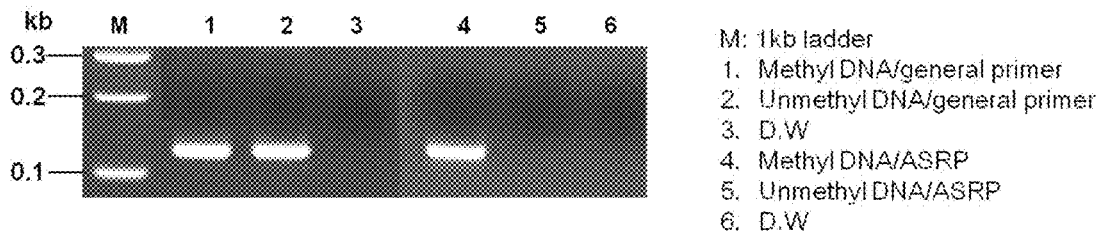
FIG. 3 shows the results of performing PCR amplification experiments using a general primer and the ASRP in order to detect methylation.

As a result, it was shown that, when the general primer was used, an amplification product appeared in both methylated SDC2 (lane 1 in FIG. 3) and unmethylated SDC2 (lane 2 in FIG. 3) even when the methylation-specific primer was used, whereas when the SDC2 methylation-specific ASRP was used, a specific amplification product was observed in methylated SDC2 (lane 4 in FIG. 3), but no amplification occurred in unmethylated SDC2 (lane 5 in FIG. 3).

INDUSTRIAL APPLICABILITY

As described above, the detection method using the allele-specific reactive primer (ASRP) according to the present invention is a technique having a very high specificity of amplification due to the characteristics of the ASRP and a proofreading DNA polymerase. The detection method can effectively detect mutations (point mutation, insertion, deletion, etc.) including a single nucleotide polymorphism (SNP), and can also be used to detect methylation of CpG after bisulfite treatment or to amplify and detect a target DNA starting with a desired nucleotide sequence from a DNA library.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for detecting a target nucleic acid, the method comprising amplifying the target nucleic acid in the presence of a DNA polymerase having proofreading activity, a reverse primer, and an allele-specific reactive primer (ASRP) which comprises i) a nucleotide sequence complementary to the target nucleic acid and ii) a nucleotide substituted with 3'-deoxynucleotide, which is located in a region from a nucleotide located right before a non-complementary nucleotide on the 5'-side of the non-complementary nucleotide,
wherein an amplification product of the target nucleic acid is produced, when the allele-specific reactive primer is complementary to the target nucleic acid, and
when the allele-specific reactive primer is not complementary to the target nucleic acid, a non-complementary nucleotide to the target nucleic acid present at the 3'end of the primer is removed by the proofreading activity of the DNA polymerase, and an amplification product of the target nucleic acid is not produced due to the 3'-deoxynucleotide remaining at the 3'end of the primer.

2. The method of claim 1, wherein the DNA polymerase having proofreading activity has 3'→5' exonuclease activity.

3. The method of claim 1, wherein a nucleotide located next to 3'-deoxynucleotide to 3'end of the allele-specific reactive primer is not removed by the proofreading activity of DNA polymerase, when the nucleotide located next to 3'-deoxynucleotide to 3'end of the allele-specific reactive primer is complementary to a target nucleic acid, and
a nucleotide located next to 3'-deoxynucleotide to 3'end of the allele-specific reactive primer is removed and thus 3'-deoxynucleotide remains at the 3' end, when the nucleotide located next to 3'-deoxynucleotide to 3'end is not complementary to the target nucleic acid.

4. The method of claim 1, comprising the steps of:
(a) mixing and hybridizing the target nucleic acid to an allele-specific reactive primer (ASRP) to obtain a hybridization product;
(b) amplifying the target nucleic acid in the hybridization product in the presence of a DNA polymerase having proofreading activity; and
(c) detecting the target nucleic acid based on the presence or absence of an amplification product of the target nucleic acid.

5. The method of claim 4, wherein the amplification in step (b) is performed by Polymerase chain reaction (PCR).

6. The method of claim 1, wherein the target nucleic acid is DNA or RNA.

7. The method of claim 1, wherein the target nucleic acid has a mutation.

8. The method of claim 7, wherein the mutation is caused by the substitution, deletion or insertion of a nucleotide of the target nucleic acid.

9. The method of claim 7, wherein an amplification product of the target nucleic acid is produced, when no mutation is present in the target nucleic acid, and
an amplification product of the target nucleic acid is not produced, when a mutation is present in the target nucleic acid.

10. The method of claim 1, wherein the target nucleic acid is a pathogen.

11. The method of claim 10, wherein the pathogen is selected from the group consisting of viruses, eubacteria, and fungi.

12. The method of claim 10, wherein an amplification product of the target nucleic acid is produced in the presence of a pathogen, and is not produced in the absence of a pathogen.

13. The method of claim 1, wherein the target nucleic acid is cytosine-methylated.

14. The method of claim 13, wherein the method for detecting the methylated target nucleic acid comprises the steps of:
  (a) chemically or enzymatically treating the target nucleic acid to covert an unmethylated cytosine nucleotide into uracil or other nucleotides without converting a methylated cytosine nucleotide;
  (b) mixing and hybridizing the chemically or enzymatically treated target nucleic acid to an allele-specific reactive primer (ASRP) to obtain a hybridization product, and amplifying the target product in the hybridization product in the presence of a DNA polymerase having proofreading activity; and
  (c) detecting methylation of the target nucleic acid based on the presence or absence of an amplification product of the target nucleic acid.

15. The method of claim 14, wherein the methylated target nucleic acid produces an amplification product, and a unmethylated target nucleic acid does not produce an amplification product.

16. A method of amplifying a target nucleic acid starting with a specific nucleotide sequence from a DNA library, the method comprising amplifying the target nucleic acid from the DNA library in the presence of a DNA polymerase having proofreading activity and an allele-specific reactive primer (ASRP) which comprises a nucleotide sequence complementary to an adaptor sequence of the DNA library at its 5' end, and
at 3' end a nucleotide sequence complementary to the target nucleic acid and a nucleotide substituted with 3'-deoxynucleotide,
wherein the target nucleic acid starting with a specific nucleotide sequence from a DNA library binds complementarily to the allele-specific reactive primer to produce an amplification product, and
when the target nucleic acid is not complementary to the allele-specific reactive primer, the non-complementary nucleotide is removed by the proofreading activity of the DNA polymerase, and an amplification product is not produced due to the remaining modified nucleotides at the 3' end.

17. The method of claim 16, wherein the DNA polymerase having proofreading activity has 3'→5' exonuclease activity.

18. The method of claim 16, wherein when a nucleotide located next to 3'-deoxynucleotide to 3'end of the allele-specific reactive primer is not removed by the proofreading activity of DNA polymerase, when the nucleotide located next to 3'-deoxynucleotide to 3'end of the allele-specific reactive primer is complementary to a target nucleic acid, and
a nucleotide located next to 3'-deoxynucleotide to 3'end of the allele-specific reactive primer is removed and thus 3'-deoxynucleotide remains at the 3' end, when the nucleotide located next to 3'-deoxynucleotide to 3' is not complementary to the target nucleic acid.

19. The method of claim 16, comprising the steps of:
  (a) randomly digesting a genomic DNA, and linking a sequencing adaptor sequence to both the 5' and 3' ends of the digested DNA fragments to prepare a DNA library;
  (b) mixing and hybridizing DNA library with an allele-specific reactive primer (ASRP), wherein the allele-specific reactive primer (ASRP) comprises a nucleotide sequence complementary to the adaptor sequencer of the DNA library and a nucleotide substituted with 3'-deoxynucleotide, which is located in a region from a nucleotide located right before a non-complementary nucleotide on the 5'-side of the non-complementary nucleotide; and
  (c) performing amplification starting from a specific nucleotide sequence in the hybridization product of the (b) in the presence of a DNA polymerase having proofreading activity.

20. The method of claim 19, wherein the amplification in step (c) is performed by polymerase chain reaction (PCR).

21. The method of claim 16, wherein only a methylated target nucleic acid is amplified.

22. The method of claim 21, wherein the method for amplification of a methylated target nucleic acid comprises the steps of:
  (a) chemically or enzymatically treating a genomic DNA to convert an unmethylated cytosine nucleotide into uracil or other nucleotides without converting a methylated cytosine nucleotide;
  (b) randomly digesting the genomic DNA, and linking a sequencing adaptor to both the 5' and 3' ends of the digested DNA fragments to construct a DNA library;
  (c) mixing and hybridizing DNA library with an allele-specific reactive primer (ASRP), wherein the ASRP comprises a nucleotide sequence complementary to the adaptor sequence of the DNA library and at the 3' end, a cytosine, a nucleotide sequence complementary to a target nucleic acid, and a nucleotide substituted with 3'-deoxynucleotide; and
  (d) amplifying a DNA fragment comprising the nucleotide sequence of a methylated target nucleic acid in the hybridization product of (c) in the presence of a DNA polymerase having proofreading activity.

23. The method of claim 22, wherein a methylated target nucleic acid is amplified and an unmethylated target nucleic acid is not amplified.

* * * * *

SEQUENCE LISTING

<160> NUMBER OF SEQ ID NOS: 10

<210> SEQ ID NO 1
<211> LENGTH: 352
<212> TYPE: DNA
<213> ORGANISM: Artificial Sequence
<220> FEATURE:
<223> OTHER INFORMATION: Nucleotide sequence for B-type Raf kinase

<400> SEQUENCE: 1

```
tatagaaatt agatctctta cctaaactct tcataatgct tgctctgata ggaaaatgag      60
atctactgtt ttcctttact tactacacct cagatatatt tcttcatgaa gacctcacag     120
taaaaatagg tgattttggt ctagctacag tgaaatctcg atggagtggg tcccatcagt     180
ttgaacagtt gtctggatcc attttgtgga tggtaagaat tgaggctatt tttccactga     240
ttaaattttt ggccctgaga tgctgctgag ttactagaaa gtcattgaag gtctcaacta     300
tagtattttc atagttccca gtattcacaa aaatcagtgt tcttattttt ta            352
```

<210> SEQ ID NO 2
<211> LENGTH: 352
<212> TYPE: DNA
<213> ORGANISM: Artificial Sequence
<220> FEATURE:
<223> OTHER INFORMATION: Nucleotide sequence for BRAF (B-type Raf
      kinase) V600E

<400> SEQUENCE: 2

```
tatagaaatt agatctctta cctaaactct tcataatgct tgctctgata ggaaaatgag      60
```

```
atctactgtt ttcctttact tactacacct cagatatatt tcttcatgaa gacctcacag    120
taaaaatagg tgattttggt ctagctacag agaaatctcg atggagtggg tcccatcagt    180
ttgaacagtt gtctggatcc attttgtgga tggtaagaat tgaggctatt tttccactga    240
ttaaattttt ggccctgaga tgctgctgag ttactagaaa gtcattgaag gtctcaacta    300
tagtattttc atagttccca gtattcacaa aaatcagtgt tcttattttt ta            352
```

```
<210> SEQ ID NO 3
<211> LENGTH: 22
<212> TYPE: DNA
<213> ORGANISM: Artificial Sequence
<220> FEATURE:
<223> OTHER INFORMATION: BRAFV600E forward primer

<400> SEQUENCE: 3
gtgattttgg tctagctaca ga                                              22

<210> SEQ ID NO 4
<211> LENGTH: 22
<212> TYPE: DNA
<213> ORGANISM: Artificial Sequence
<220> FEATURE:
<223> OTHER INFORMATION: BRAFV600E forward allele-specific reactive
      primer (ASRP)

<400> SEQUENCE: 4
gtgattttgg tctagctaca ga                                              22

<210> SEQ ID NO 5
<211> LENGTH: 23
<212> TYPE: DNA
<213> ORGANISM: Artificial Sequence
<220> FEATURE:
<223> OTHER INFORMATION: BRAFV600E reverse primer

<400> SEQUENCE: 5
ttctagtaac tcagcagcat ctc                                             23

<210> SEQ ID NO 6
<211> LENGTH: 350
<212> TYPE: DNA
<213> ORGANISM: Artificial Sequence
<220> FEATURE:
<223> OTHER INFORMATION: Methylation SDC2 (Syndecan-2) nucleotide
      sequence

<400> SEQUENCE: 6
aaattagaaa ttgaatttcg gtacgggaaa ggagttcgcg gaggagtaaa attatagtag     60
agtaagaaga gttttagaga gtagtttttt cggagtatta atttcgtgtc gggagtgtag    120
aaattaataa gtgagagggc gtcgcgtttt cggggcgtag ttgcgggcgg cgggagtagg    180
cgtaggagga ggaagcgagc gttttcgagt ttcgagttcg agttttcgag tttgagtcgt    240
aatcgttgcg gtattttgtt tcggattcgt gtgcgcgggt tgcgtcgagc gttgggtagg    300
aggtttcgtt ttgtttttggt tgtaagtagc ggttgggagt agtcggtttt              350

<210> SEQ ID NO 7
<211> LENGTH: 350
<212> TYPE: DNA
<213> ORGANISM: Artificial Sequence
<220> FEATURE:
<223> OTHER INFORMATION: Unmethylated SDC2 nucleotide sequence

<400> SEQUENCE: 7
```

-continued

```
aaattagaaa ttgaattttg gtatgggaaa ggagtttgtg gaggagtaaa attatagtag        60
agtaagaaga gttttagaga gtagtttttt tggagtatta attttgtgtt gggagtgtag       120
aaattaataa gtgagagggt gttgtgtttt tggggtgtag ttgtgggtgg tgggagtagg       180
tgtaggagga ggaagtgagt gttttgagt tttgagtttg agttttgag tttgagttgt        240 aattgttgtg gtattttgtt ttggatttgt gtgtgtgggt tgtgttgagt gttgggtagg      300
aggttttgtt ttgttttggt tgtaagtagt ggttgggagt agttggtttt                350
```

<210> SEQ ID NO 8
<211> LENGTH: 23
<212> TYPE: DNA
<213> ORGANISM: Artificial Sequence
<220> FEATURE:
<223> OTHER INFORMATION: Methylated SDC2 forward general primer

<400> SEQUENCE: 8
tagaaattaa taagtgagag ggc                                              23

<210> SEQ ID NO 9
<211> LENGTH: 23
<212> TYPE: DNA
<213> ORGANISM: Artificial Sequence
<220> FEATURE:
<223> OTHER INFORMATION: Methylated SDC2 forward ASRP primer

<400> SEQUENCE: 9
tagaaattaa taagtgagag ggc                                              23

<210> SEQ ID NO 10
<211> LENGTH: 19
<212> TYPE: DNA
<213> ORGANISM: Artificial Sequence
<220> FEATURE:
<223> OTHER INFORMATION: Methylated SDC2 reverse primer

<400> SEQUENCE: 10
gactcaaact cgaaaactc                                                   19